United States Patent [19]

Bianchi

[11] 4,045,501

[45] Aug. 30, 1977

[54] METHOD FOR MAKING o- AND p-HALOALKYL STYRENES

[75] Inventor: Thomas A. Bianchi, Irondequoit, N.Y.

[73] Assignee: Eastman Kodak Company, Rochester, N.Y.

[21] Appl. No.: 601,870

[22] Filed: Aug. 4, 1975

Related U.S. Application Data

[60] Division of Ser. No. 391,180, Aug. 24, 1973, Pat. No. 3,927,117, which is a continuation-in-part of Ser. No. 237,902, March 27, 1972, abandoned.

[51] Int. Cl.$^2$ .............................................. C07C 25/14
[52] U.S. Cl. ........................ 260/651 R; 260/651 HA; 260/613 D
[58] Field of Search .................... 260/651 R, 651 HA

[56] References Cited

U.S. PATENT DOCUMENTS

| 2,780,604 | 2/1957 | Clark et al. | 260/651 HA |
|---|---|---|---|
| 3,067,182 | 12/1962 | Jones | 260/651 HA |

*Primary Examiner*—C. Davis
*Attorney, Agent, or Firm*—E. W. Milan

[57] ABSTRACT

A method for making o- and p- halomethyl styrenes which comprises reacting an ethyl benzene, paraformaldehyde and hydrogen halide, treating the reaction product with a halogen, and dehydrohalogenating the resulting o- and p- halomethyl (1-haloethyl) benzenes at an elevated temperature using as dehydrohalogenating agent an amine acceptor of the generic formula:

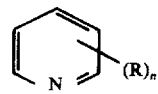

wherein R is an alkyl group of 1 to 6 carbon atoms, $n$ is an integer having a value of from 1 to 5, and at least one alkyl group is attached to a carbon atom adjacent to the nitrogen atom and when $n$ is more than 1, the alkyl groups may be the same or different groups, and recovering a mixture of o- and p- halomethyl styrenes.

12 Claims, No Drawings

METHOD FOR MAKING O- AND P- HALOALKYL STYRENES

This is a division of application Ser. No. 391,180 filed Aug. 24, 1973, now U.S. Pat. No. 3,927,117, which is a continuation-in-part of application Ser. No. 237,902 filed Mar. 27, 1972, and now abandoned.

FIELD OF THE INVENTION

The invention relates generally to certain substituted styrenes and more particularly to the preparation of 3,4-dialkoxy styrenes and haloalkyl styrenes by dehydrohalogenation.

BACKGROUND OF THE INVENTION

It has been proposed that 3,4-dialkoxy styrenes (substituted styrenes) be prepared by dehydrohalogenating chloro-1-(3,4-dialkoxyphenyl)ethanes using pyridine as the dehydrohalogenating reagent. In the prior art, 3,4-(dimethoxy)styrenes have also been prepared by the thermal dehydration of 1-(3,4-dimethoxyphenyl)ethanol and by methylation of 4-hydroxy-3-methoxy styrene with methyl iodide or dimethyl sulfate. These methods have not been entirely satisfactory because the yields are rather low. Very low yields are obtained in the dehydrohalogenation process because of the formation of the quaternary salt of pyridine with the chloro compound. The thermal dehydration process is also relatively expensive because of the high temperature required for the reaction.

It has also been proposed that haloalkyl styrenes be prepared by at least partially dehydrohalogenating halogenated haloalkylphenyl ethanes using pyridine as the dehydrohalogenating reagent. These styrenes have also been prepared by haloalkylating styrene. The same disadvantages that the use of pyridine presents in its use in preparing dialkoxy styrenes occur in such methods.

SUMMARY OF THE INVENTION

It is therefore an object of the present invention to provide a process for preparing substituted styrenes in improved yields. Another object of the present invention is to provide a process for making 3,4-(dialkoxy)styrenes and haloalkyl styrenes at improved yields. A further object of this invention is to provide reagents for dehydrohalogenating halogenated 1-(dialkoxyphenyl)ethane. A still further object of the present invention is to provide reagents for dehydrohalogenating halogenated haloalkylphenyl ethanes. An additional object of this invention is to provide a process for preparing 3,4-(dimethoxy)styrene. A further object of the present invention is to provide a process for preparing chloromethylstyrene, and especially p-chloromethylstyrene.

These and other objects and advantages of this invention are obtained by dehydrohalogenating halogenated 1-(dialkoxyphenyl)ethane or a halogenated haloalkylphenyl ethane using as the dehydrohalogenating reagent an amine acceptor of the generic formula:

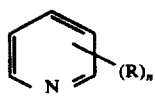

wherein R is an alkyl group of 1 to 6 carbon atoms, $n$ is an integer having a value of from 1 to 5, and at least one alkyl group is attached to a carbon atom adjacent to the nitrogen atom and when $n$ is more than 1, the alkyl groups may be the same or different groups.

DETAILED DESCRIPTION OF PREFERRED EMBODIMENTS

The substituted styrenes prepared according to the process of this invention correspond to the following formulae I and II:

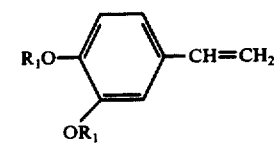

I.

wherein each $R_1$ is an alkyl radical of 1 to 4 carbon atoms and preferably methyl;

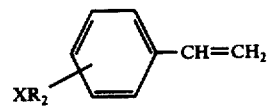

II.

wherein $R_2$ is an alkylene radical of 1 to 4 carbon atoms and preferably methylene, and X is a halogen atom selected from the group consisting of chlorine, bromine, and iodine, and preferably is chlorine.

In a stepwise method of preparation of the substituted styrenes, a 1-(3,4-dialkoxyphenyl)ethanol wherein each alkoxy moiety has 1 to 4 carbon atoms may be used as a starting material to prepare a compound of formula I. In the preferred embodiment, 1-(3,4-dimethoxyphenyl)ethanol is used. The starting material is converted in step (1) to its intermediate halogen derivative by reacting it with a suitable halogenating agent. Suitable halogenating agents are, for example, in chlorination, thionyl chloride; in bromination, hydrogen bromide, thionyl bromide, or phosphorus tribromide; in iodination, the standard iodinating agents, e.g. $I_2$. For example, 1-(3,4-dimethoxyphenyl)ethanol is converted to 1-chloro-1-(3,4-dimethoxyphenyl)ethane by reaction with thionyl chloride.

The halogen derivative is then in step (2) dehydrohalogenated by reaction with an amine acceptor of the generic formula:

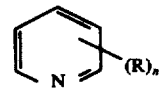

wherein R is an alkyl group of 1 to 6 carbon atoms, $n$ is an integer having a value of from 1 to 5, and at least one alkyl group is attached to a carbon atom closest to the nitrogen atom and when $n$ is more than 1, the alkyl groups may be the same or different groups, as the dehydrohalogenating reagent to prepare the formula I compound.

Examples of amine acceptors according to this generic formula are 2,6-lutidine, s-collidine, and 2-picoline. Preferably, an excess of the amine acceptor is used to keep the reaction basic throughout, thereby avoiding the risk of polymerization which takes place in the presence of acid. Other suitable materials may be used to keep the reaction basic.

Preferably, the dialkoxy compound is treated in a process wherein steps (1) and (2) are combined and the dialkoxy compound, the halogenating agent, and the amine acceptor are all placed in the same container at the same time. Thus, in the preferred reaction, the dialkoxy compound is treated in such a combination process with thionyl chloride in the presence of two molar equivalents of 2,6-lutidine. The dialkoxy compound is thus converted to the intermediate halogen derivative, the chloro derivative in the preferred reaction, which is substantially simultaneously dehydrohalogenated to the substituted styrene product of formula I.

The above-described methods are further illustrated by the following reactions:

A filtrate is obtained from which the product is obtained.

In the method of preparation of the substituted styrenes of formula II, an alkyl benzene, wherein the alkyl group has 1 to 6 carbon atoms, may be used as a starting material. In the preferred embodiment it is ethyl benzene. The starting material is coverted in step (1) to its halogen derivative in a stepwise process by reacting the alkyl benzene with a mixture of para-formaldehyde and a halogenating agent to give a mixture of ortho- and para-(haloalkyl-phenyl)alkane. For example, ethyl benzene is converted to o- and p- chloromethyl phenyl ethane (chloromethylethyl benzene) by reaction with hydrogen chloride. These o- and p-(haloalkylphenyl)e-

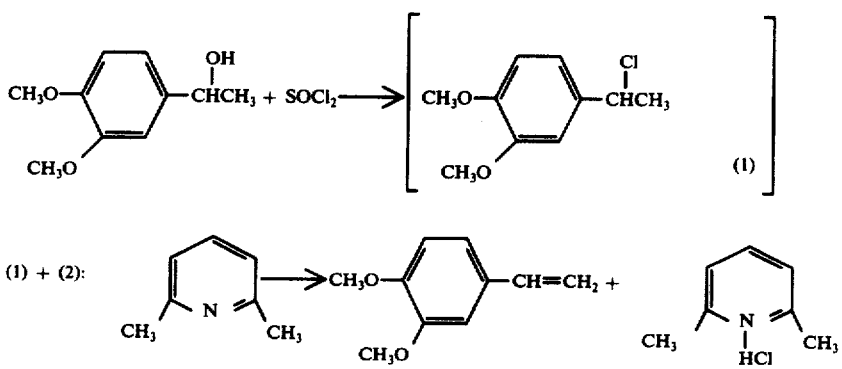

The thionyl chloride and dialkoxy compound used to prepare the intermediate compound (1) are present in about equal molar quantities. The reaction is carried out in a reaction medium such as benzene. Any suitable reaction medium may be used so long as it does not interfere with the reaction. Other mediums which may be used are toluene, xylene, and chloroform. The thionyl chloride is added to a mixture of benzene and 2,6-lutidine. To this mixture which has been stirred is added the 1-(3,4-dimethoxyphenyl)ethanol while the temperature is held at from about 5° C to about 20° C, and preferably at about 10° C. A thick slurry is obtained and heated to about 20° C to about 90° C and preferably to about 80° C. While the above temperatures are preferred, higher or lower temperatures may also be used.

thanes are then further halogenated by a suitable halogenating reagent. For example, the p-chloromethylethyl benzene compound above is converted to p-chloromethyl(1-bromoethyl)benzene and its ortho isomer by bromination. These halogen derivatives are then dehydrohalogenated by reaction in a step (2) with an amine acceptor as set out above.

Preferably, the haloalkylphenyl ethane compound is treated with an equimolar amount of the amine acceptor.

The substituted styrenes of formula II can also be prepared in a combination process substantially as described above.

The above-described methods for preparation of the compounds of formula II are further illustrated by the following reactions:

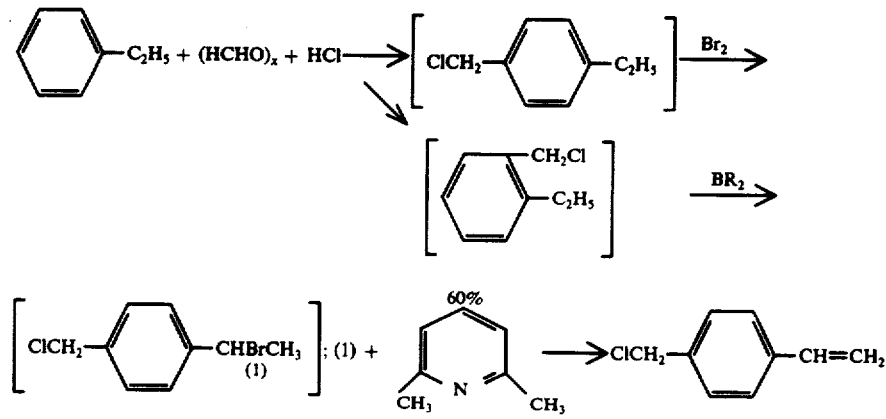

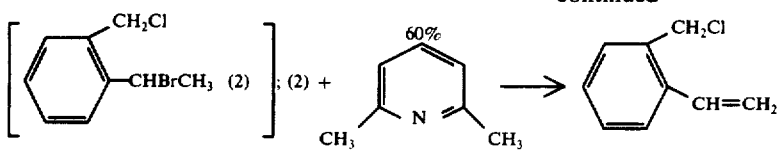

The following examples will further illustrate the process of this invention.

EXAMPLE 1

In a 1-liter flask set in an ice bath and equipped with a stirrer, condenser, and dropping funnel were placed 85 gm. (0.8 mole) of 2,6-lutidine and 450 ml of benzene. The mixture was stirred and cooled in the ice bath at 0° C, and 39 gm. (0.33 mole) of thionyl chloride were added from the dropping funnel in 30 minutes holding the temperature below 10° C. To this stirred mixture were added 60 gm. (0.33 mole) of 1-(3,4-dimethoxyphenyl)ethanol dropwise in 1 hour, holding the temperature below 10° C. The resulting thick slurry was heated slowly to reflux and was maintained at the reflux temperature (80° C) for 3 hours. The mixture was stirred overnight at room temperature. In the morning, the insoluble 2,6-lutidine hydrochloride was recovered on a filter. The benzene filtrate was washed with water, a 10% solution of sodium carbonate, and finally again with water. After separation, the benzene-product layer was dried over anhydrous sodium sulfate, and filered. The solution was stabilized by the addition of 5 gm. of 6-tert-butyl-m-cresol. The mixture was distilled and, after removal of the benzene, the product, 3,4-(dimethoxy)styrene, boiling at 122°-4°/9mm, was collected. The product was stabilized with approximately 100ppm. of 6-tert-butyl-m-cresol. The yield was 35 gm., which is 65% of the theoretical amount of 54 gm.

EXAMPLE 2

In a flask were mixed 2.30 ml. of benzene and 48 gm. pyridine (0.61 mole). The mixture was cooled below 5° and 33 gm. (0.28 mole) of thionyl chloride were added in 15 minutes. The solution was warmed to 20° C and 50 gm. (0.28 mole) of 1-(3,4-dimethoxyphenyl)ethanol in 50 ml. of benzene were added at 20°-30° C over a period of 2 hours. The solution was stirred at room temperature overnight.

The slurry was heated to reflux for 2 hours and cooled. The liquors then were separated from the solid (or oil) present. After washing with benzene, the amine hydrochloride by-product was discarded. The benzene solution was washed twice with water and once with a dilute sodium carbonate solution. It was then heated at reflux over flake sodium hydroxide. The benzene was removed in vacuo, and the residual oil was diluted with ethyl ether. Amine hydrochloride precipitated and was removed by filtration. The filtrate was concentrated to an oil containing 3,4-(dimethoxy)styrene product, inhibited with a small amount of 2,6-di-tertbutyl-p-cresol, and distilled through a short column using an oil vacuum pump. The product was identified by its infra-red spectrum. The yield was only 7 gm. or only 15% of its theoretical weight of 46 gm.

The following examples show use of other amine acceptors that can be used in practicing the process of this invention.

EXAMPLES 3-6

In carrying out Examples 3 through 6, the process of Example 2 was conducted with the amine acceptor, pyridine, being replaced by amine acceptors according to this invention. It is to be noted that the yields are about 3 to 4.5 times greater when an amine acceptor of the invention is used instead of pyridine.

| Example | Amine Acceptor | Yield |
|---|---|---|
| 3 | 2,6-lutidine | 51% |
| 4 | s-collidine | 58% |
| 5 | 2-picoline | 60% |
| 6 | 2-picoline | 69% |

EXAMPLE 7

This example shows how the process can be utilized in the preparation of other substituted styrenes.

Ortho- and para-chloromethylstyrenes were prepared in the following manner. Ethyl benzene was chloromethylated with a mixture of para-formaldehyde and hydrochloride to give a ratio of 40 to 60 isomeric mixture of ortho- and para-chloromethylethylbenzenes (by nuclear magnetic resonance (NMR) analysis). The yield of the ortho-para mixture was 60-70%.

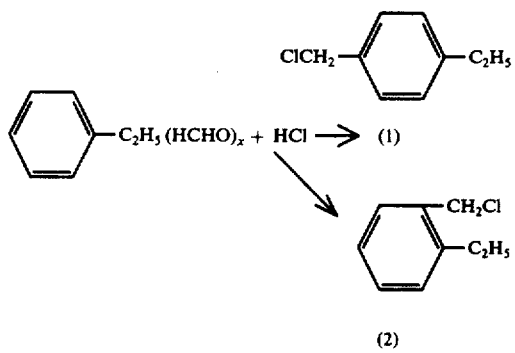

Bromination of this mixture gave nearly quantitative yields of p-chloromethyl(1-bromoethyl)benzene and its ortho isomer.

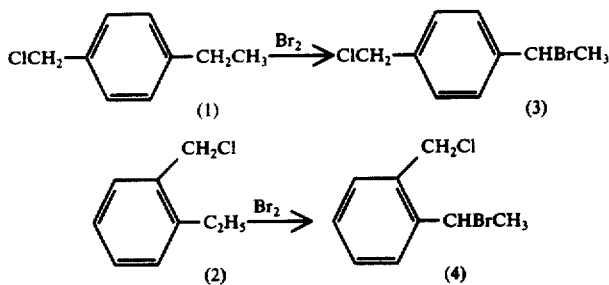

The dehydrohalogenation step was carried out by brominating the crude isomeric mixture, isolating it by removing the solvent under vacuum, and treating the brominated isomeric mixture with an equimolar amount (based on theory) of 2,6-lutidine at 90° C. The reaction was exothermic, and was considered complete at the end of the exotherm. The reaction mixture was cooled, washed with water and dilute hydrochloric acid, extracted with benzene, and filtered. The benzene was removed by distillation. The crude product was distilled using a short Vigreaux column at 100°-150° C/15mm. and pure product was obtained in 60% yield. The product was a mixture of ortho and para isomers of chloromethyl styrene in a ratio of 40 to 60% as determined by NMR.

It can be seen from the foregoing that substituted styrenes in highly improved yields can be obtained by the process of this invention. The compounds are useful as monomers for polymerization. Also, 3,4-(dimethoxy) styrene may also be used as an orange juice preservative.

The invention has been described in detail with particular reference to preferred embodiments thereof, but it will be understood that variations and modifications can be effected within the spirit and scope of the invention.

What is claimed is:

1. In a method for making o- and p-chloromethylstyrenes comprising the steps of mixing ethyl benzene, paraformaldehyde and hydrogen chloride and reacting said mixture with bromine to form a mixture of o- and p-chloromethyl(1-bromoethyl) benzenes, the improvement which comprises: heating and dehydrobrominating said o- and p- chloromethyl(1-bromoethyl) benzenes with an equimolar amount of an amine acceptor of the formula

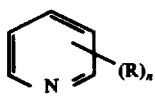

wherein R is alkyl of 1 to 6 carbon atoms, n is an integer of 1 to 5 and at least one alkyl is attached to a carbon atom adjacent the nitrogen atom in said formula, provided that the alkyls may be the same or different where, n is more than 1; whereby a mixture of said o- and p-chloromethyl styrenes is formed.

2. A method according to claim 1 wherein the amine acceptor is 2-picoline.

3. A method according to claim 1 wherein the amine acceptor is s-collidine.

4. A method according to claim 1 wherein the amine acceptor is 2,6-lutidine.

5. In a method for making a mixture of ortho- and parahalomethyl styrenes represented by the generic formula

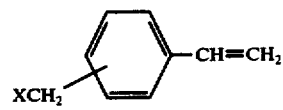

wherein X is a halogen atom selected from the group consisting of chlorine, bromine, and iodine, comprising:
 i. reacting an ethyl benzene, para-formaldehyde, and hydrogen halide to form a mixture of ortho- and para-(halomethylphenyl)ethanes, and
 ii. halogenating said mixture from (i) with a halogenating agent selected from thionyl chloride, hydrogen bromide, thionyl bromide, phosphorus tribromide and iodine to form a mixture of ortho- and para-halomethyl (1-haloethyl)benzenes, the improvement which comprises:
 iii. heating and dehydrohalogenating said mixture from (ii) using as the dehydrohalogenating agent an amine acceptor of the generic formula

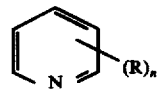

wherein R is an alkyl group of 1 to 6 carbon atoms, n is an integer having a value of from 1 to 5 and at least one alkyl group is attached to a carbon atom adjacent to the nitrogen atom, and when n is more than 1; the alkyl groups may be the same or different groups, and
 iv. recovering a mixture of ortho- and para- halomethyl styrenes from the reaction mass.

6. A method according to claim 5 wherein the (halomethylphenyl)ethane is ortho or parachloromethylphenyl ethane.

7. A method according to claim 5 wherein the amine acceptor is 2,6-lutidine.

8. A method according to claim 5 wherein the amine acceptor is s-collidine.

9. A method according to claim 5 wherein the amine acceptor is 2-picoline.

10. A method according to claim 5 wherein the hydrogen halide is hydrogen chloride.

11. A method according to claim 5 wherein the halogenating agent is bromine.

12. A method according to claim 7 wherein the hydrogen halide is hydrogen chloride and the halogenating agent is bromine.

* * * * *